United States Patent

Palmer

[11] Patent Number: 5,119,968
[45] Date of Patent: Jun. 9, 1992

[54] TRASH BAG DISPENSER

[76] Inventor: Tarry R. Palmer, 1220-G Airport Freeway #471, Bedford, Tex. 76022

[21] Appl. No.: 689,457

[22] Filed: Apr. 22, 1991

[51] Int. Cl.⁵ ............................................. B65H 3/58
[52] U.S. Cl. .................................. 221/26; 221/27; 206/554; 428/905
[58] Field of Search ............... 206/493, 554; 221/26, 221/27, 199; 428/905

[56] References Cited

U.S. PATENT DOCUMENTS

| | | | |
|---|---|---|---|
| 2,774,531 | 12/1956 | Rosenthal | 428/905 X |
| 3,285,406 | 11/1966 | Winesett | |
| 3,285,407 | 11/1966 | Abramson | 206/493 |
| 3,318,444 | 5/1967 | Weicher et al. | 206/493 |
| 3,341,003 | 9/1967 | Marsh | 221/26 X |
| 3,353,661 | 11/1967 | Membrino | 206/493 X |
| 4,201,299 | 5/1980 | Bumgarner et al. | |
| 4,207,984 | 6/1980 | Kelly et al. | 206/554 |
| 4,349,104 | 9/1982 | Hayes | 428/905 X |
| 4,654,256 | 3/1987 | Doree et al. | 428/905 X |
| 4,769,264 | 9/1988 | Dreger | 428/905 X |
| 4,848,929 | 7/1989 | Rawl | 428/905 X |
| 4,865,371 | 9/1989 | Egberg | 428/905 X |

Primary Examiner—Robert P. Olszewski
Assistant Examiner—Dean A. Reichard
Attorney, Agent, or Firm—Rogers, Howell & Haferkamp

[57] ABSTRACT

A scented trash bag dispenser is comprised of a plurality of disposable trash bags arranged in an ordered stack and connected by a frangible connection to a base member. The base member is connectable to a separate object or surface to suspend the stacked plurality of trash bags from the object or surface, where the forward most trash bag of the plurality of bags is easily accessible for use. Either or both of the base member and plurality of trash bags are constructed of a material that emits an air freshening scent to perfume the air in the vicinity of the trash bag dispenser.

8 Claims, 1 Drawing Sheet

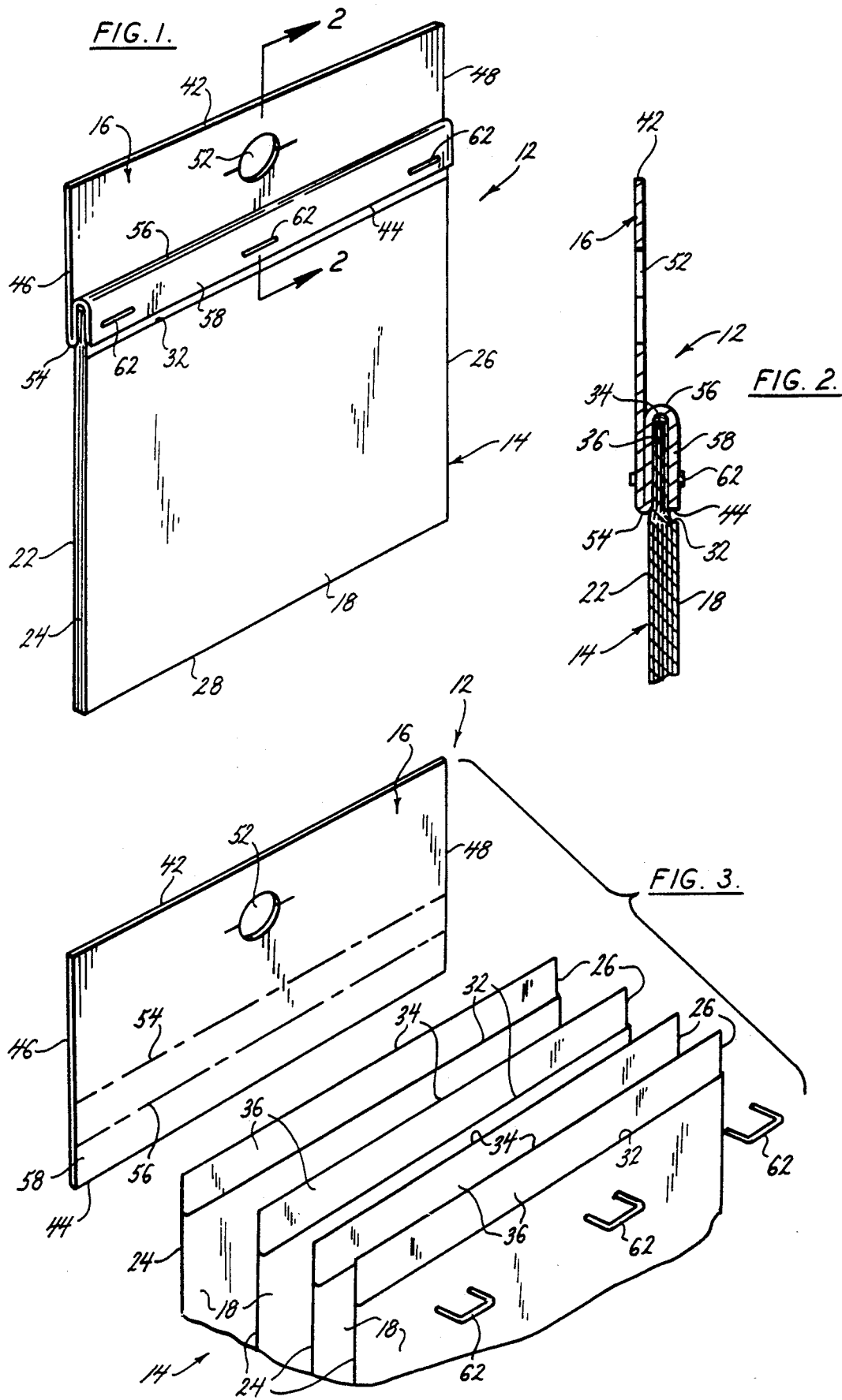

TRASH BAG DISPENSER

BACKGROUND OF THE INVENTION

(1) Field of the Invention

The present invention relates to a scented trash bag dispenser.

In particular, the present invention relates to a trash bag dispenser comprising a plurality of disposable trash bags arranged in an ordered stack and connected to a base member by a frangible connection. The base member is connectable to a separate object or surface to suspend the stacked plurality of trash bags from the object or surface, where the top most trash bag in the plurality is accessible for use. Either or both of the base member and plurality of trash bags are constructed of a material that emits an air freshening scent to perfume the air in the vicinity of the invention.

(2) Description of the Related Art

Singular trash bags provided with some method of suspending the trash bag from an object or surface so that the interior of the trash bag is easily accessible are known in the prior art. Examples of these types of trash bags are the bags given out by gas stations and car washes that are suspended from a radio dial of an automobile to provide an easily accessible trash bag in the automobile interior. Similar types of trash bags are used in the home and workplace. These types of prior art trash bags are disadvantaged in that they do not provide a great deal of space for trash, and must be frequently emptied or replaced during their use. Each time the bag is filled it must be disassembled from its attachment to the automobile radio dial or other object in the home or workplace suspending the bag, emptied or disposed of, and then reassembled or replaced by a new bag on the radio dial or other object. Moreover, this type of trash bag is often used in the automobile, home, or workplace to dispose of food items. If the food items remain in the trash bag for an extended period of time, they will likely begin to produce odors. To eliminate the odors the trash bag must be disposed of or emptied, often before the trash bag has been completely filled.

What is needed to overcome these disadvantages associated with prior art trash bags is a plurality of separate trash bags that are connected in an ordered stack, and are suspended from an object or surface in a manner that provides easy access to the top most trash bag of the ordered stack. The bags would be easily torn away from the stack and disposed of when filled. This would eliminate the need for emptying or replacing a single bag. To eliminate the odors that are often produced by trash disposed of in the bags, the stacked plurality of bags would be constructed of a material that emits an air freshening scent that would mask any odors produced by trash disposed of in the bags.

SUMMARY OF THE INVENTION

The scented trash bag dispenser of the present invention is generally comprised of a plurality of separate receptacles or trash bags that are arranged in an ordered stack and are releasably secured to a base member. Either or both of the base member and plurality of trash bags are constructed of a material that emits an air freshening or perfumed scent. The air freshening scent masks any odors produced by trash placed in one of the bags. The dispenser is designed to be equally useful in an automobile, in the home, or in the workplace.

Each bag of the plurality of trash bags is a rectangular bag having at least a front and a back wall. The bags could be given a variety of shapes other than rectangular. The front and back walls are secured along their side edges and their bottom edge. In alternate embodiments of the invention, pleated or folded side and bottom walls may be provided between the side and bottom edges of the front and back walls of each bag. The top edges of the front and back bag walls are left separate from each other and together define an opening into the interior of the bag. The top most edge of the back wall of each bag extends slightly above the top most edge of the front wall of each bag, forming a tab or strip that extends completely across the width of the bag. In alternate embodiments, the tab or strips could extend across only a portion of the back wall width. The strip or tab is employed in securing each bag of the stacked plurality of bags to the base member.

The base member is a substantially flat rectangular member having a top end and a bottom end and a width substantially equal to the width of the plurality of bags. An aperture is provided through the base member adjacent its top end. The aperture is employed in suspending the base member and the plurality of bags from an object or surface by inserting the object or some type of projection on the surface through the aperture. Several folds are provided across the width of the base member at its bottom end. The folds form a downward projecting flap of the base member that extends across the entire width of the base member. The strips or tabs along the top most edges of the bag back walls are positioned adjacent the base member flap and the flap is folded over the back wall top portions so that the back wall top portion of each of the plurality of bags is positioned beneath the flap. The flap covering the bag strips is provided for appearance purposes and could be eliminated. Several staples are then driven through the flap, the top portions of the bag back walls, and through the folded over portion of the base member to secure the stacked plurality of bags to the base member. The staples provide a frangible connection between the bags and the base member that enables the top most bag of the plurality of bags to be easily torn away from the staples and disposed of when filled. A line of perforations may be provided across the strips or tabs along the top edges of the bag back walls to facilitate separating the top most bag from the plurality of bags. Tearing the top most bag from the staples or along the perforations exposes for use the next bag of the plurality of bags directly below the top most bag.

As stated above, either the base member, the plurality of bags, or both may be constructed of a material that emits an air freshening or perfumed scent to mask the odors of any trash deposited in the bags.

BRIEF DESCRIPTION OF THE DRAWINGS

Further objects and features of the present invention are revealed in the following detailed description of the preferred embodiment of the invention and in the drawing figures wherein:

FIG. 1 is a perspective view of the scented trash bag dispenser of the invention;

FIG. 2 is a segmented side elevation view, in section, of the scented trash bag dispenser of the invention taken along the line 2—2 of FIG. 1; and FIG. 3 is a segmented, exploded view of the component parts of the scented trash bag dispenser of the invention.

DESCRIPTION OF THE PREFERRED EMBODIMENT

The scented trash bag dispenser 12 of the present invention is shown in FIG. 1. The dispenser 12 is generally comprised of a plurality of separate receptacles or trash bags 14 and a base member 16. As an option, either or both of the base member and the plurality of trash bags are constructed of a material that emits an air freshening or perfumed scent. The scent emitting material masks odors of any trash deposited in the bags. The embodiment of the invention shown in the drawing figures will be described as being used in the interior of an automobile, however, the dispenser 12 is designed to be used in a variety of different embodiments other than that disclosed.

As seen in FIGS. 1 and 3, each bag of the plurality of trash bags 14 is a rectangular bag having at least a front wall 18 and a back wall 22. The bag could also be given a variety of shapes other than rectangular. As shown, the front and back walls are secured along their left 24 and right sides 26 and along their common bottom edges 28. In a variant embodiment of the invention, pleated or folded side walls and bottom walls (not shown) may be provided between the side edges 24, 26 and the bottom edge 28 of the front and back walls of each back to increase the interior volume of the bag.

As seen in FIG. 3, the top edges of the front and back walls 32, 34 of the bags are left unattached and separate from each other. The top most edge 34 of the back wall 22 of each bag extends slightly above the top most edge 32 of the front wall 18 of each bag, forming a tab or strip 36 that extends completely across the width of each bag. The strip or tab 36 is employed in securing each of the bags of the stacked plurality of bags to the base member 16 in a manner to be described. In an alternate embodiment of the invention, a line of perforations (not shown) is provided across the back walls of the bags. The perforations extend transversely across the back wall of each bag just behind the top edge 32 of the front wall 18 of each bag. The line of perforations separates the strip or tab 36 at the top of each bag back wall from the remainder of the bag back wall.

The base member 16 is a substantially flat rectangular member having a top edge 42, a bottom edge 44, and left and right side edges 46, 48. As seen in the drawing figures, the width of the base member is substantially equal to the width of the plurality of bags 14. An aperture 52 is provided through the center of the base member adjacent its top edge 42. The aperture is provided to be used in suspending the base member and the plurality of bags from an object or surface by inserting the object or some type of projection on the surface through the aperture. One example is inserting an automobile radio dial through the aperture 52 to suspend the plurality of bags in the automobile's interior. Several folds 54, 56 are provided across the width of the base member 16 adjacent its bottom edge 44. The folds are used to form a downward projecting flap 58 at the bottom edge 44 of the base member that extends across the entire width of the base member. The flap 58 is employed in connecting the plurality of bags 14 to the base member 16 in a manner to be explained.

In connecting the plurality of bags 14 to the base member 16, the bottom edge 44 of the base member is first folded upward along the fold line 54. The bottom edge 44 of the base member is then again folded downward over the fold line 56 to give the base member the folded configuration shown in FIGS. 1 and 2. The top edges 34 of the bag back walls are inserted beneath the flap 58 of the base member so that the edges 34 abut along the inside of fold 56 and the strips or tabs 36 are overlapped by the base member flap 58. The flap is provided primarily for appearance purposes and could be eliminated without effecting the functioning of the invention. Several staples 62 are driven through the flap 58, the bag strips 36, and the folded over portions of the base member 16 behind the strips. The staples secure the stacked plurality of bags 14 to the base member 16 and enable the bag strips 36 to be easily torn away from the staples to separate a used bag from the stacked plurality of bags. In this manner, the staples provide a frangible connection between the bags and the base member that enables the forward most bag of the plurality of bags to be easily torn away from the staples and disposed of when filled.

In the alternate embodiment of the invention employing a line of perforations across the strips 36 of the bags, the forward most bag of the plurality of bags is easily torn away from the line of perforations to separate the forward most bag from the plurality of bags when filled. Tearing the forward most bag from the staples or along the line of perforations exposes the next bag of the plurality of bags directly behind the forward most bag for use.

The forward most bag is filled by inserting a finger behind the top edge 32 of the bag front wall 18 and pulling the top edge forward away from the base member 16 to expand the opening of the bag. With the flap 58 holding the back wall 22 of the bag against the base member 16, trash can then be easily inserted through the opening between the bag front and back walls. When the forward most bag is filled, it is then easily torn away from its frangible connection to the base member 16 and disposed of. Tearing away the forward most bag of the plurality of bags exposes the next bag in the stack for use.

While the present invention has been described by reference to a specific embodiment, it should be understood that modifications and variations of the invention may be constructed without departing from the scope of the invention defined in the following claims.

I claim:

1. A receptacle dispenser supporting a plurality of receptacles and providing access to a receptacle of the plurality of receptacles, the dispenser comprising:

a substantially flat base member, the base member having first and second vertically spaced, parallel fold lines extending horizontally across the base member, the base member being formed with a downward folded flap between the first fold line and a bottom edge of the base member, and with an upward folded flap between the second fold line and the first fold line, the downward folded flap overlapping the upward folded flap;

a plurality of substantially flat receptacles, each receptacle of the plurality of receptacles having a front wall and a back wall that lie flat against each other, and each receptacle of the plurality of receptacles having an opening between the front and back walls that enables the front wall to be separated from the back wall and provides access to an interior of the receptacle through the opening, each receptacle of the plurality of receptacles lying substantially flat over each other in an ordered stack; and, a connection means for connecting the plurality of receptacles to the base member, the connection means connecting the downward folded base member flap to the upward folded base member flap and connecting the plurality of receptacles to the base member between the overlapping downward folded flap and upward folded flap, the connection means enabling successive receptacles of the plurality of receptacles to be separated from the plurality of receptacles and the base member by pulling successive receptacles from the base member.

2. The dispenser of claim 1, wherein:
both the base member and the plurality of receptacles are constructed of a material that emits an air freshening scent.

3. The dispenser of claim 1, wherein:
the base member is constructed of a material that emits an air freshening scent.

4. The dispenser of claim 1, wherein:
the plurality of receptacles are constructed of a material that emits an air freshening scent.

5. The dispenser of claim 1, wherein:
top ends of the back walls of each of the plurality of receptacles extend above top ends of the front walls of the receptacles, and the downward folded flap and the upward folded flap of the base member overlap over the top ends of the back walls of the plurality of receptacles.

6. The dispenser of claim 5, wherein:
the connection means includes at least one staple extending through the base member downward folded flap and the upward folded flap and the top ends of the plurality of receptacle back walls, the staple enabling successive receptacles of the plurality of receptacles to be separated from the plurality of receptacles and the base member by tearing the top ends of the back walls of the receptacles from the staple.

7. The dispenser of claim 5, wherein:
a line of perforations is provided across the top ends of the back walls of the plurality of receptacles, the line of perforations enabling successive receptacles to be separated from the plurality of receptacles and the base member by tearing the receptacle back walls along the line of perforations.

8. The dispenser of claim 1, wherein:
the base member is provided with an aperture for attaching the base member to an object by inserting the object through the aperture, the aperture being positioned on the base member vertically above the upward folded flap and downward folded flap of the base member.

* * * * *